United States Patent
Kwan et al.

(10) Patent No.: US 10,489,620 B2
(45) Date of Patent: Nov. 26, 2019

(54) SYSTEM AND APPARATUS FOR ASSESSING SANITIZATION COMPLIANCE

(71) Applicant: WiSilica Inc., Laguna Hills, CA (US)

(72) Inventors: Dennis Ching Chung Kwan, San Diego, CA (US); Suresh Kumar Singamsetty, Aliso Viejo, CA (US)

(73) Assignee: WiSilica Inc., Laguna Hills, CA (US)

( * ) Notice: Subject to any disclaimer, the term of this patent is extended or adjusted under 35 U.S.C. 154(b) by 0 days.

(21) Appl. No.: 15/813,152

(22) Filed: Nov. 14, 2017

(65) Prior Publication Data

US 2018/0218184 A1 Aug. 2, 2018

Related U.S. Application Data

(60) Provisional application No. 62/421,628, filed on Nov. 14, 2016.

(51) Int. Cl.
| | |
|---|---|
| *G06K 19/06* | (2006.01) |
| *G06K 7/10* | (2006.01) |
| *H04W 84/18* | (2009.01) |
| *G06K 19/077* | (2006.01) |
| *H04W 4/80* | (2018.01) |
| *H04W 4/029* | (2018.01) |
| *G08B 21/24* | (2006.01) |
| *G06Q 10/06* | (2012.01) |
| *G06Q 50/22* | (2018.01) |
| *G06Q 50/26* | (2012.01) |
| *H04L 29/08* | (2006.01) |
| *A47K 5/12* | (2006.01) |

(52) U.S. Cl.
CPC ..... *G06K 7/10475* (2013.01); *G06K 7/10297* (2013.01); *G06K 19/07762* (2013.01); *G06Q 10/0639* (2013.01); *G06Q 10/06398* (2013.01); *G06Q 50/22* (2013.01); *G06Q 50/26* (2013.01); *G08B 21/245* (2013.01); *H04W 4/029* (2018.02); *H04W 4/80* (2018.02); *H04W 84/18* (2013.01); *A47K 5/1217* (2013.01); *H04L 67/1093* (2013.01)

(58) Field of Classification Search
CPC ......... G06K 19/07762; G06K 7/10297; G06K 7/10475; H04L 67/1093; H04W 84/18
USPC ....................................................... 235/492
See application file for complete search history.

(56) References Cited

U.S. PATENT DOCUMENTS

| | | | | |
|---|---|---|---|---|
| 7,423,533 | B1 * | 9/2008 | LeBlond | G08B 21/245 340/572.1 |
| 8,285,564 | B2 * | 10/2012 | Perkins | G06Q 10/06 705/2 |
| 2006/0056370 | A1 * | 3/2006 | Hancock | H04B 7/2606 370/338 |
| 2006/0109084 | A1 * | 5/2006 | Yarvis | H04L 67/12 340/10.1 |
| 2007/0157385 | A1 * | 7/2007 | Lemire | A61G 7/005 5/600 |

(Continued)

*Primary Examiner* — Thien M Le
(74) *Attorney, Agent, or Firm* — Rowan TELS LLC (57) ABSTRACT

A system and apparatus for assessing whether a personnel has complied with sanitation protocols. The system may incorporate wearable tags on each personnel which can communicate with a mesh network to confirm presence of the personnel. In an embodiment, a soap dispenser may be part of the mesh network such that, when the dispenser is activated, a personnel's presence is detected and recorded.

7 Claims, 12 Drawing Sheets

(56) References Cited

U.S. PATENT DOCUMENTS

| | | | |
|---|---|---|---|
| 2008/0099043 A1* | 5/2008 | Barnhill | A46B 13/02 134/6 |
| 2008/0181132 A1* | 7/2008 | Underhill | H04L 12/1818 370/254 |
| 2011/0047876 A1* | 3/2011 | Houser | A47K 5/06 49/70 |
| 2011/0068892 A1 | 3/2011 | Perkins et al. | |
| 2011/0316703 A1* | 12/2011 | Butler | G08B 21/245 340/573.1 |
| 2013/0257614 A1 | 10/2013 | Perkins | |
| 2015/0186693 A1 | 7/2015 | Blair et al. | |
| 2016/0271659 A1* | 9/2016 | Russ | A61B 7/00 |
| 2017/0017815 A1* | 1/2017 | Caso | G06K 7/10257 |
| 2017/0270481 A1* | 9/2017 | Morgenthau | H04W 4/029 |
| 2017/0303187 A1* | 10/2017 | Crouthamel | H04W 4/80 |
| 2018/0218184 A1 | 8/2018 | Kwan et al. | |

* cited by examiner (PRIOR ART)

SYSTEM AND APPARATUS FOR ASSESSING SANITIZATION COMPLIANCE

CROSS-REFERENCE TO RELATED APPLICATIONS

This present disclosure claims the benefit of U.S. Provisional Application Ser. No. 62/421,628, filed on Nov. 14, 2016.

BACKGROUND

Some conventional personnel sanitization systems may utilize a manual logging process that relies on "honor" policies by the persons being sanitized, leading to inaccurate determinations of the actual sanitization of these persons. Other conventional methods may utilize sensors to determine the number of persons meeting or exceeding a cleanliness threshold, and/or determining the amount of dispensed sanitization substance used (in theory) by these persons. This method does not identify any persons that are in non-compliance with sanitization thresholds.

There is thus a need for a system that determines when sanitization dispensing should occur, whether the dispensing occurred, and the identity of the person performing the dispensing.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Firmware" in this context refers to software logic embodied as processor-executable instructions stored in read-only memories or media.

"Hardware" in this context refers to logic embodied as analog or digital circuitry.

"Logic" in this context refers to machine memory circuits, non-transitory machine readable media, and/or circuitry which by way of its material and/or material-energy configuration comprises control and/or procedural signals, and/ or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Programmable device" in this context refers to an integrated circuit designed to be configured and/or reconfigured after manufacturing. The term "programmable processor" is another name for a programmable device herein. Programmable devices may include programmable processors, such as field programmable gate arrays (FPGAs), configurable hardware logic (CHL), and/or any other type programmable devices. Configuration of the programmable device is generally specified using a computer code or data such as a hardware description language (HDL), such as for example Verilog, VHDL, or the like. A programmable device may include an array of programmable logic blocks and a hierarchy of reconfigurable interconnects that allow the programmable logic blocks to be coupled to each other according to the descriptions in the HDL code. Each of the programmable logic blocks may be configured to perform complex combinational functions, or merely simple logic gates, such as AND, and XOR logic blocks. In most FPGAs, logic blocks also include memory elements, which may be simple latches, flip-flops, hereinafter also referred to as "flops," or more complex blocks of memory. Depending on the length of the interconnections between different logic blocks, signals may arrive at input terminals of the logic blocks at different times.

"Software" in this context refers to logic implemented as processor-executable instructions in a machine memory (e.g. read/write volatile or nonvolatile memory or media).

Wireless mesh nodes that may utilize the disclosed embodiments may implement various wireless protocols, including but not limited to:

"6LowPAN": an acronym of IPv6 (Internet Protocol Version 6) over Low power Wireless Personal Area Networks. It is a wireless standard for low-power radio communication applications that need wireless internet connectivity at lower data rates for devices with limited form factor. 6LoWPAN utilizes the RFC6282 standard for header compression and fragmentation. This protocol is used over a variety of networking media including Bluetooth Smart (2.4 GHz) or ZigBee or low-power RF (sub-1 GHz) and as such, the data rates and range may differ based on what networking media is used.

"Bluetooth Low-Energy (BLE)—or Bluetooth Smart": a wireless personal area network technology aimed at reduced power consumption and cost while maintaining a similar communication range as traditional Bluetooth. Like traditional Bluetooth, the frequency utilized is 2.4 GHz (ISM-Industrial, Scientific and Medical), the maximum range is generally 50-150 m with data rates up to 1 Mbps.

"Cellular": a communication network where the last link is wireless. The network is distributed over land areas called cells and utilizes one of the following standards GSM/GPRS/EDGE (2G), UMTS/HSPA (3G), LTE (4G). Frequencies are generally one of 900/1800/1900/2100 MHz. Ranges are 35 km max for GSM; 200 km max for HSPA and typical data download rates are: 35-170 kps (GPRS), 120-384 kbps (EDGE), 384 Kbps-2 Mbps (UMTS), 600 kbps-10 Mbps (HSPA), 3-10 Mbps (LTE).

"LoRaWAN": Low Power Wide Area Network, a media access control (MAC) protocol for wide area networks for low-cost, low-power, mobile, and secure bi-directional communication for large networks of up to millions of devices. LoRaWAN is employed on various frequencies, with a range of approximately 2-5 km (urban environment) to 15 km (suburban environment) and data rates of 0.3-50 kbps.

"NFC": "Near Field Communication" and is a subset of RFID (Radio Frequency Identifier) technology. NFC is standardized in ECMA-340 and ISO/IEC 18092. It employs electromagnetic induction between two loop antennae when NFC devices are within range (10 cm). NFC utilizes the frequency of 13.56 MHz (ISM). Data rates range from 106 to 424 kbit/s.

"SigFox": a cellular-style system that enables remote devices to connect using ultra-narrow band (UNB) technology and binary phase-shift keying (BPSK) to encode data. Utilizes the 900 MHz frequency and has a range of 30-50 km in rural environments and 3-10 km in urban environments with data rates from 10-1000 bps.

"Thread": a wireless mesh network standard that utilizes IEEE802.15.4 for the MAC (Media Access Control) and Physical layers, IETF IPv6 and 6LoWPAN (IVP6). Thread operates at 250 kbps in the 2.4 GHz band. The IEEE 802.15.4-2006 version of the specification is used for the Thread stack.

"Weightless": an open machine to machine protocol which spans the physical and mac layers. Operating frequency: 200 MHz to 1 GHz (900 MHz (ISM) 470-790 MHz (White Space)) Fractional bandwidth of spectrum band: <8% (for continuous tuning). Range up to 10 km and data Rates which range from a few bps up to 100 kbps "WiFi": a wireless network standard based on 802.11 family which consists of a series of half-duplex over-the-air modulation techniques that use the same basic protocol. Frequencies utilized include 2.4 GHz and 5 GHz bands with a range of approximately 50 m. Data rate of 600 Mbps maximum, but 150-200 Mbps is more typical, depending on channel frequency used and number of antennas (latest 802.11-ac standard should offer 500 Mbps to 1 Gbps).

"Z-Wave": a wireless standard for reliable, low-latency transmission of small data packets. The Z-Wave utilizes the Z-Wave Alliance ZAD12837/ITU-T G.9959 standards and operated over the 900 MHz frequency in the US (Part 15 unlicensed ISM) and is modulated by Manchester channel encoding. Z-Wave has a range of 30 m and data rates up to 100 kbit/s.

"ZigBee": a wireless networking standard for low power, low data rate, and lost cost applications. The Zigbee protocol builds upon the Institute of Electrical and Electronics Engineers (IEEE) 802.15.4 standard which defines a short range, low power, low data rate wireless interface for small devices that have constrained power, CPU, and memory resources. Zigbee operates over the 2.4 GHz frequency, with a range of 10-100 m and data rates of 250 kbps.

A mesh network is a type of machine communication system in which each client node (sender and receiver of data messages) of the network also relays data for the network. All client nodes cooperate in the distribution of data in the network. Mesh networks may in some cases also include designated router and gateway nodes (e.g., nodes that connect to an external network such as the Internet) that are or are not also client nodes. The nodes are often laptops, cell phones, or other wireless devices. The coverage area of the nodes working together as a mesh network is sometimes called a mesh cloud.

Mesh networks can relay messages using either a flooding technique or a routing technique. Flooding is a routing algorithm in which every incoming packet, unless addressed to the receiving node itself, is forwarded through every outgoing link of the receiving node, except the one it arrived on. With routing, the message is propagated through the network by hopping from node to node until it reaches its destination. To ensure that all its paths remain available, a mesh network may allow for continuous connections and may reconfigure itself around broken paths. In mesh networks there is often more than one path between a source and a destination node in the network. A mobile ad hoc network (MANET) is usually a type of mesh network. MANETs also allow the client nodes to be mobile.

A wireless mesh network (WMN) is a mesh network of radio nodes. Wireless mesh networks can self-form and self-heal and can be implemented with various wireless technologies and need not be restricted to any one technology or protocol. Each device in a mobile wireless mesh network is free to move, and will therefore change its routing links among the mesh nodes accordingly.

Mesh networks may be decentralized (with no central server) or centrally managed (with a central server). Both types may be reliable and resilient, as each node needs only transmit as far as the next node. Nodes act as routers to transmit data from nearby nodes to peers that are too far away to reach in a single hop, resulting in a network that can span larger distances. The topology of a mesh network is also reliable, as each node is connected to several other nodes. If one node drops out of the network, due to hardware failure or moving out of wireless range, its neighbors can quickly identify alternate routes using a routing protocol.

Figure 1:
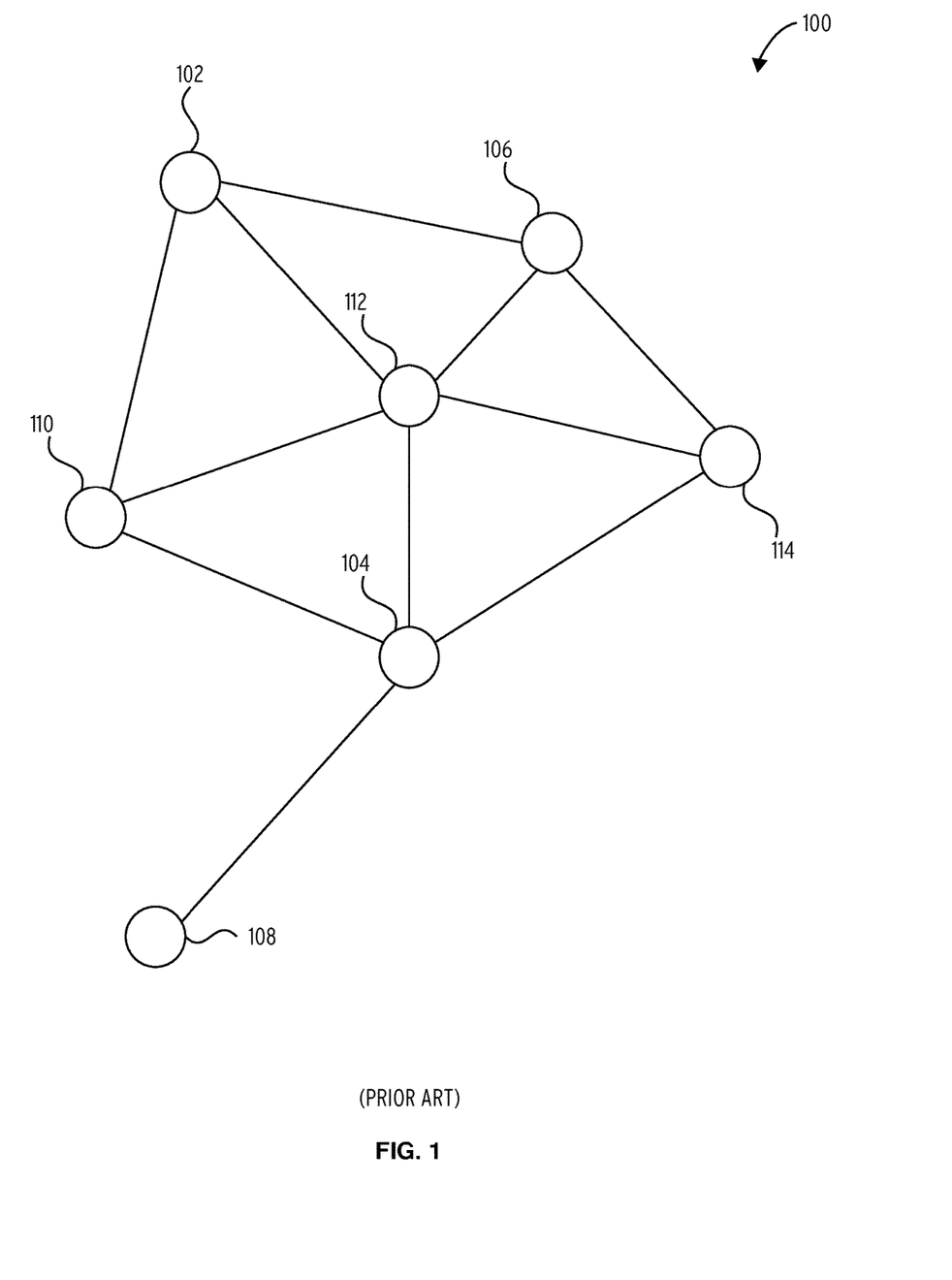
FIG. 1 illustrates a wireless mobile mesh network 100 in accordance with one embodiment.

Referring to FIG. 1, an embodiment of a wireless mobile mesh network 100 includes a server node 102, a router node 110, a router node 112, a router node 106, a router node 104, a gateway node 114, and a gateway node 108. The server node 102, the gateway node 114, and the gateway node 108 also operate as router nodes. Every node in the network participates in the routing of communications in the wireless mobile mesh network 100. The gateway node 114 and gateway node 108 provide an interface between the wireless mobile mesh network 100 and an external network, such as the Internet or a local area network. The server node 102 provides some level of centralized management for the wireless mobile mesh network 100, and may be optional if each node acts autonomously to self-manage. One or more of the nodes may be fixed in location, some of the nodes may be mobile, or all of the nodes may be mobile.

Figure 2:
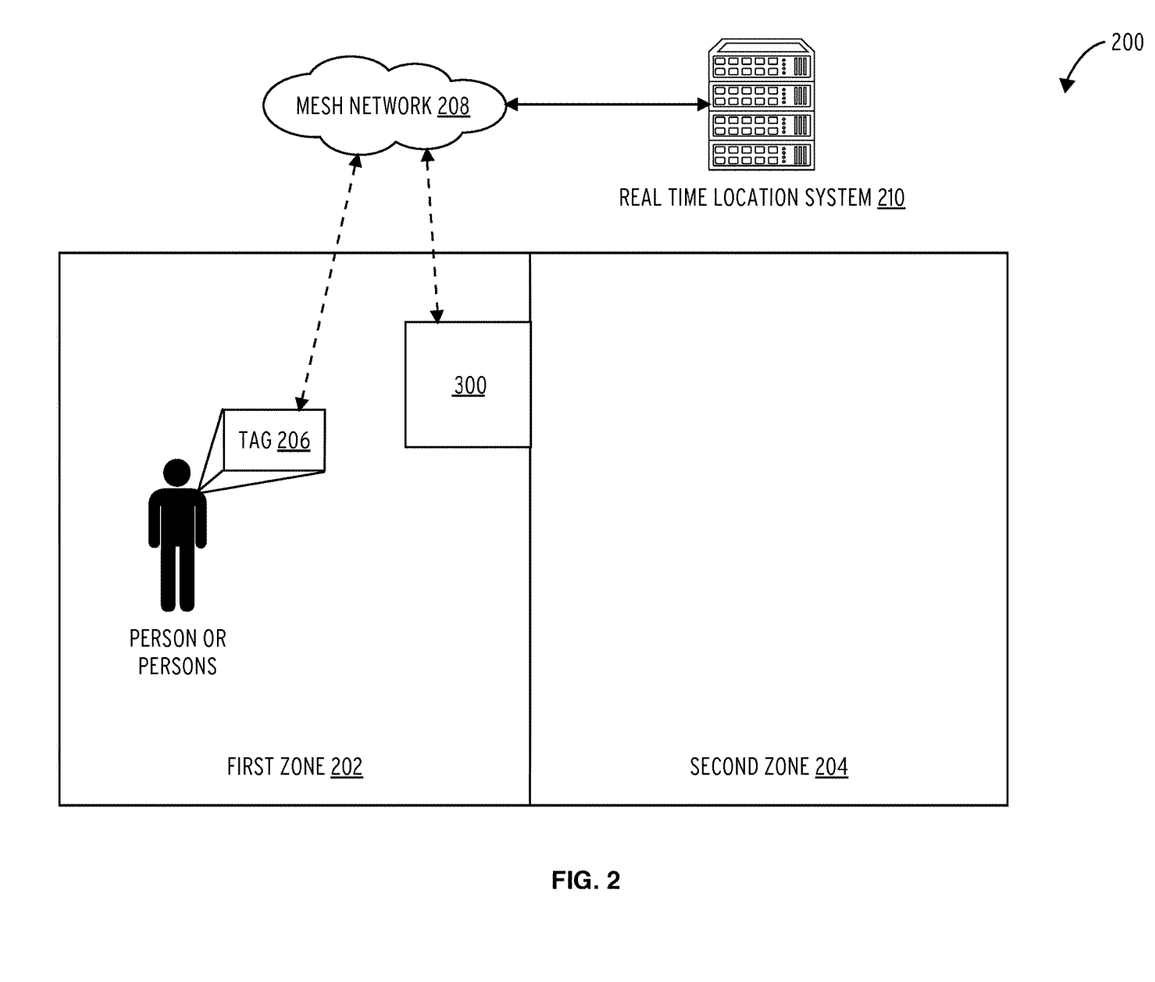
FIG. 2 illustrates an embodiment of a sanitization verification system 200.

Referring to FIG. 2, the sanitization verification system 200 includes a first zone 202, a second zone 204, a tag 206, a mesh network 208, a real time location system 210, and a sanitization device 300. The mesh network 208 may be organized as depicted for example in FIG. 8. The real time location system 210 may be organized as depicted for example in FIG. 9, FIG. 10, and FIG. 11.

The first zone 202 and the second zone 204 may be physical locations. The first zone 202 may be designated as a dirty zone, while the second zone 204 may be designated a clean zone. A person or persons moving from the first zone 202 to the second zone 204 may utilize the sanitization device 300 to maintain cleanliness of the person or persons and the second zone 204.

The sanitization device 300 may provide a signal to the mesh network 208 in response to being activated. The mesh network 208 may, in response, be altered from a low-activity state (i.e., sleep state) to a high-activity receive state (i.e., awake state). The mesh network 208 in the high-activity receive state may receive a signal sent from the tag 206. The mesh network 208 may return to the low-activity state after a period of time, which may be a fixed value or may be dynamically determined by the real time location system 210 based on the signals received from the sanitization device 300 and the tag 206. One embodiment of the sanitization device 300 is further described in conjunction with FIG. 3.

The tag 206 may provide a periodic signal to the mesh network 208. The signal may comprise identification and a received signal strength indicator (RSSI) of the tag 206. The tag 206 may be affixed to a person or persons. The tag 206 may utilize Bluetooth low energy (BLE). The RSSI may be utilized to determine a proximity to the sanitization device 300.

The mesh network 208 may receive signals from the sanitization device 300 and the tag 206. The signals may alter the state of the mesh network 208 as discussed above. The mesh network 208 may also filter signals received to the signals emitted by the tag 206 based on the location of the the tag 206 (e.g., utilizing the identification number of each tag 206). The mesh network 208 may send signals to the sanitization device 300, the tag 206, and the real time location system 210.

The real time location system 210 may receive signals from the mesh network 208. The signals may be utilized to determine the location of the tag 206, whether the tag 206 moved from the first zone 202 to the second zone 204, and the proximity of the tag 206 to the sanitization device 300.

Figure 3:
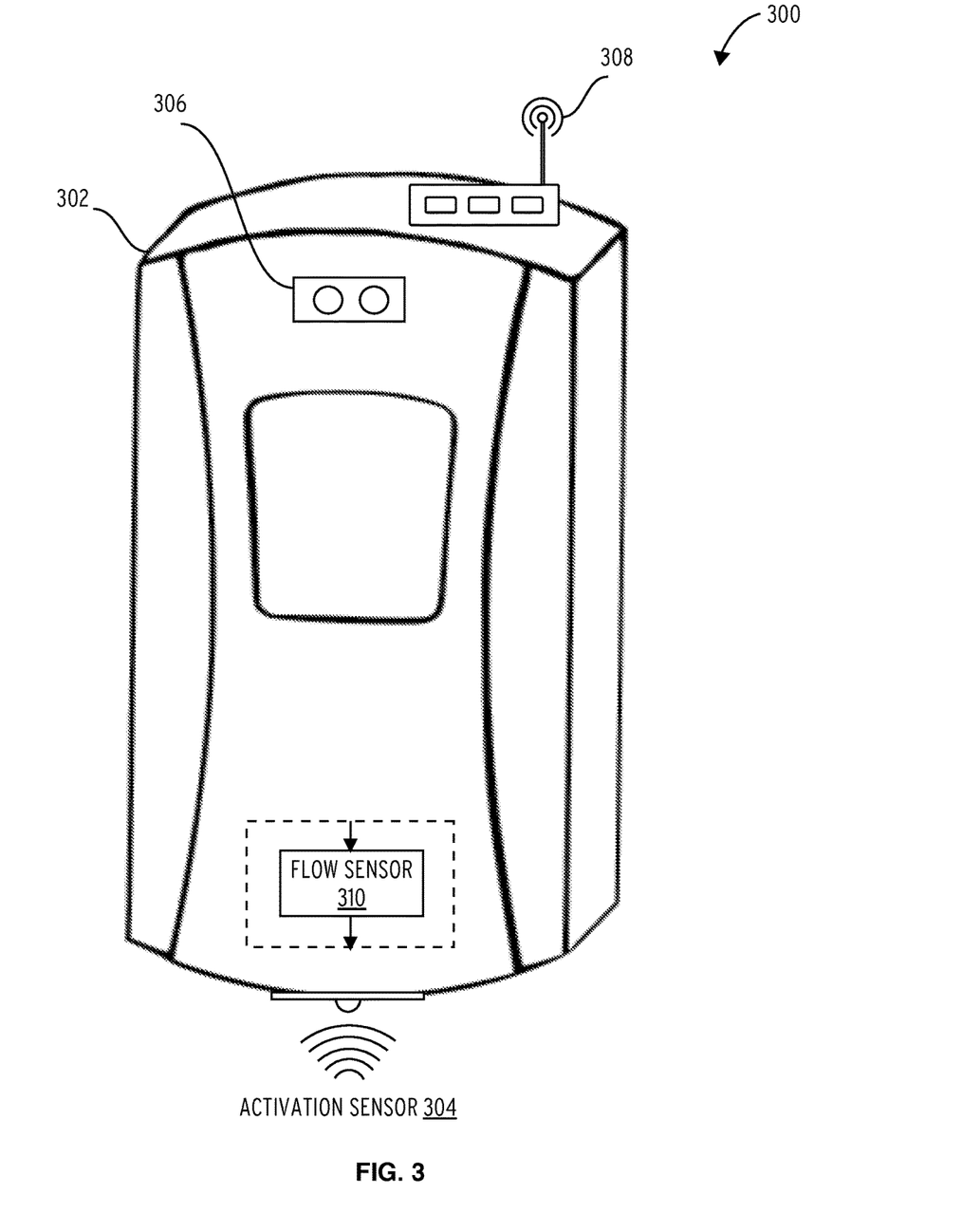
FIG. 3 illustrates an embodiment of a sanitization device 300.

Referring to FIG. 3, an embodiment of a sanitization device 300 includes a housing 302, an activation sensor 304, a notification device 306, a signal transmitter 308, and a flow quantity measurement sensor 310. The sanitization device 300 is a specific type of wireless mess mesh network node 402 as illustrated for example in FIG. 4.

The sanitization device 300 may dispense a cleaning agent. The cleaning agent may be stored in the housing 302 or an inner compartment of the housing 302 and dispensed upon operation of the activation sensor 304. The cleaning agent may take the form of a gel, foam, or liquid solution and may comprise chemicals, such as isopropyl alcohol (isopropanol), ethanol, n-propanol, or povidone-iodine. The cleaning agent may also include water or an aerosol.

As noted activation may occur via the activation sensor 304, which may utilize a proximity sensor, mechanical action, haptic input, or other familiar mechanisms. The activation sensor 304 may utilize an infrared sensor and may be integrated into the sanitization device 300, or may be external to but coupled with the sanitization device 300.

The notification device 306 may activate in response to the dispensing of the cleaning agent and may record said dispensing event and how much cleaning agent was dispensed. The notification device 306 may be a light-emitting diode. In other embodiments, the notification device 306 may emit light or sound, or activate a mechanism that provides visual, audible, or tactile feedback. The signal transmitter 308 may send a signal to the mesh network 208, which may occur in response to the activation sensor 304 being activated. The flow quantity measurement sensor 310 may measure the amount of the cleaning agent dispensed. The flow quantity measurement sensor 310 may measure the flow of cleaning agent directly; record the number of activations, which may then be utilized to determine the amount of the cleaning agent dispensed; and/or measure the amount of the cleaning agent prior to and after an activation of the sanitization device 300. The flow quantity measurement sensor 310 may then send a signal to the mesh network 208. The sanitization device 300, the activation sensor 304, the notification device 306, the signal transmitter 308, and the flow quantity measurement sensor 310 may be battery-operated, incorporate a low-power state, be waterproof, and/or comprise hygienic seals.

Figure 4:
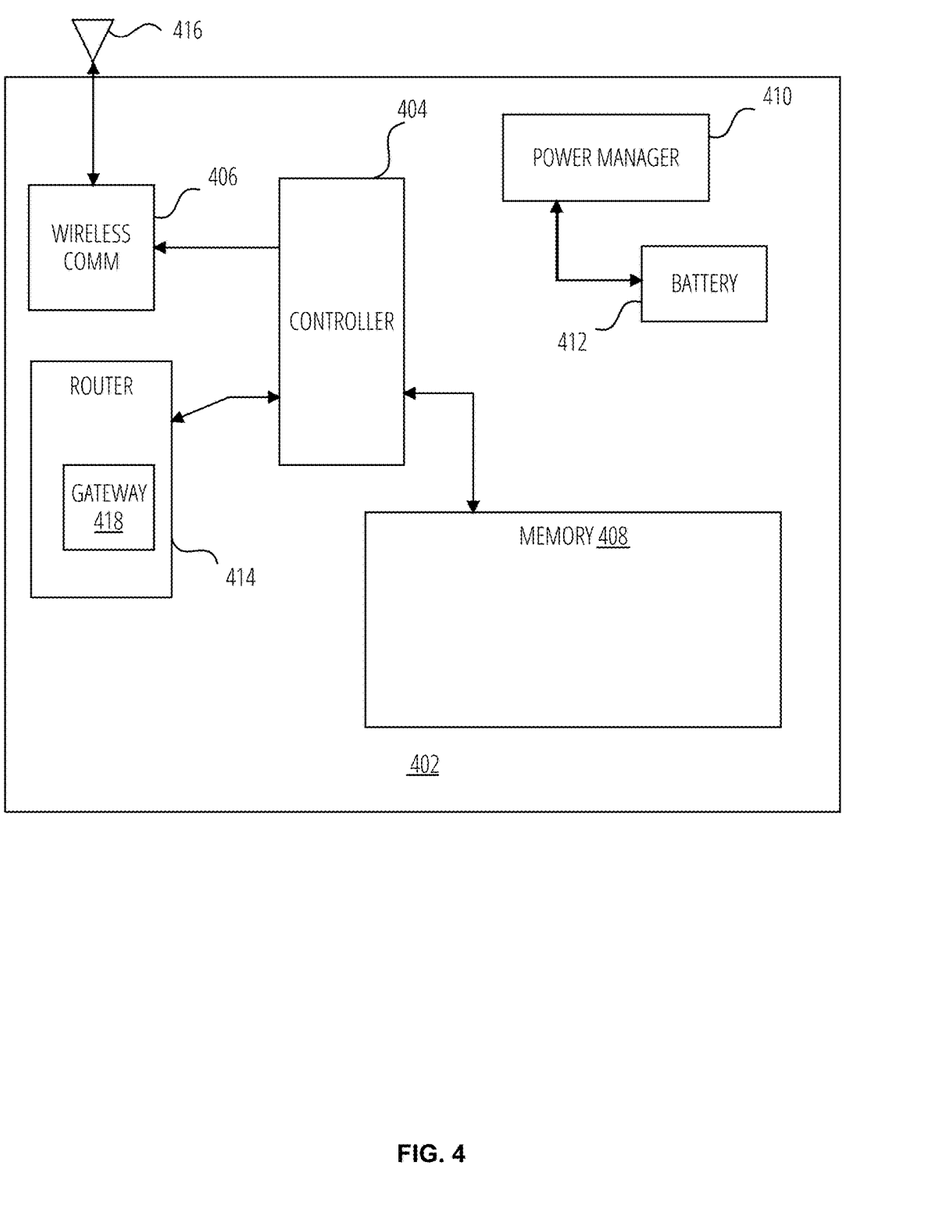
FIG. 4 illustrates an embodiment of a wireless mess mesh network node 402.

Referring to FIG. 4, a wireless mess mesh network node 402 includes an antenna 416, a signal processing and system control 404, a wireless communication 406, a memory 408, a power manager 410, a battery 412, a router 414, a wireless mess mesh network node 402, and a gateway 418.

The memory 408 may comprise logic to implement aspects of the processes described herein.

The signal processing and system control 404 controls and coordinates the operation of other components as well as providing signal processing for the wireless mess mesh network node 402. For example the signal processing and system control 404 may extract baseband signals from radio frequency signals received from the wireless communication 406 logic, and process baseband signals up to radio frequency signals for communications transmitted to the wireless communication 406 logic. The signal processing and system control 404 may comprise a central processing unit, digital signal processor, one or more controllers, or combinations of these components.

The wireless communication 406 includes memory 408 which may be utilized by the signal processing and system control 404 to read and write instructions (commands) and data (operands for the instructions).

The router 414 performs communication routing to and from other nodes of a mesh network (e.g., wireless mobile mesh network 100) in which the wireless mess mesh network node 402 is utilized. The router 414 may optionally also implement a network gateway 418.

The components of the wireless mess mesh network node 402 may operate on power received from a battery 412. The battery 412 capability and energy supply may be managed by a power manager 410.

The wireless mess mesh network node 402 may transmit wireless signals of various types and range (e.g., cellular, WiFi, BlueTooth, and near field communication i.e. NFC). The wireless mess mesh network node 402 may also receive these types of wireless signals. Wireless signals are transmitted and received using wireless communication 406 logic coupled to one or more antenna 416. Other forms of electromagnetic radiation may be used to interact with proximate devices, such as infrared (not illustrated).

Figure 5:
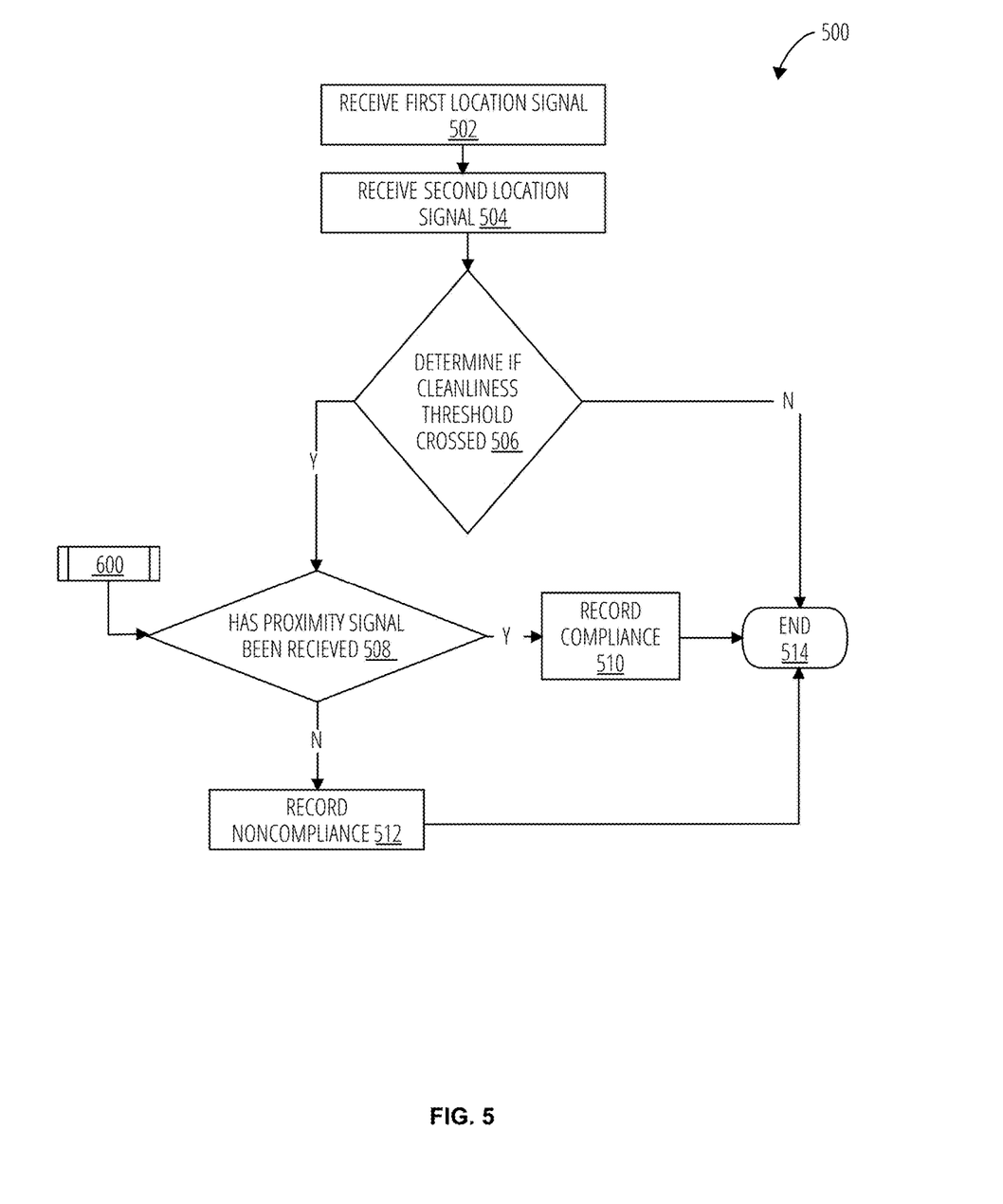
FIG. 5 illustrates an embodiment of a sanitization verification process 500.
Figure 11:
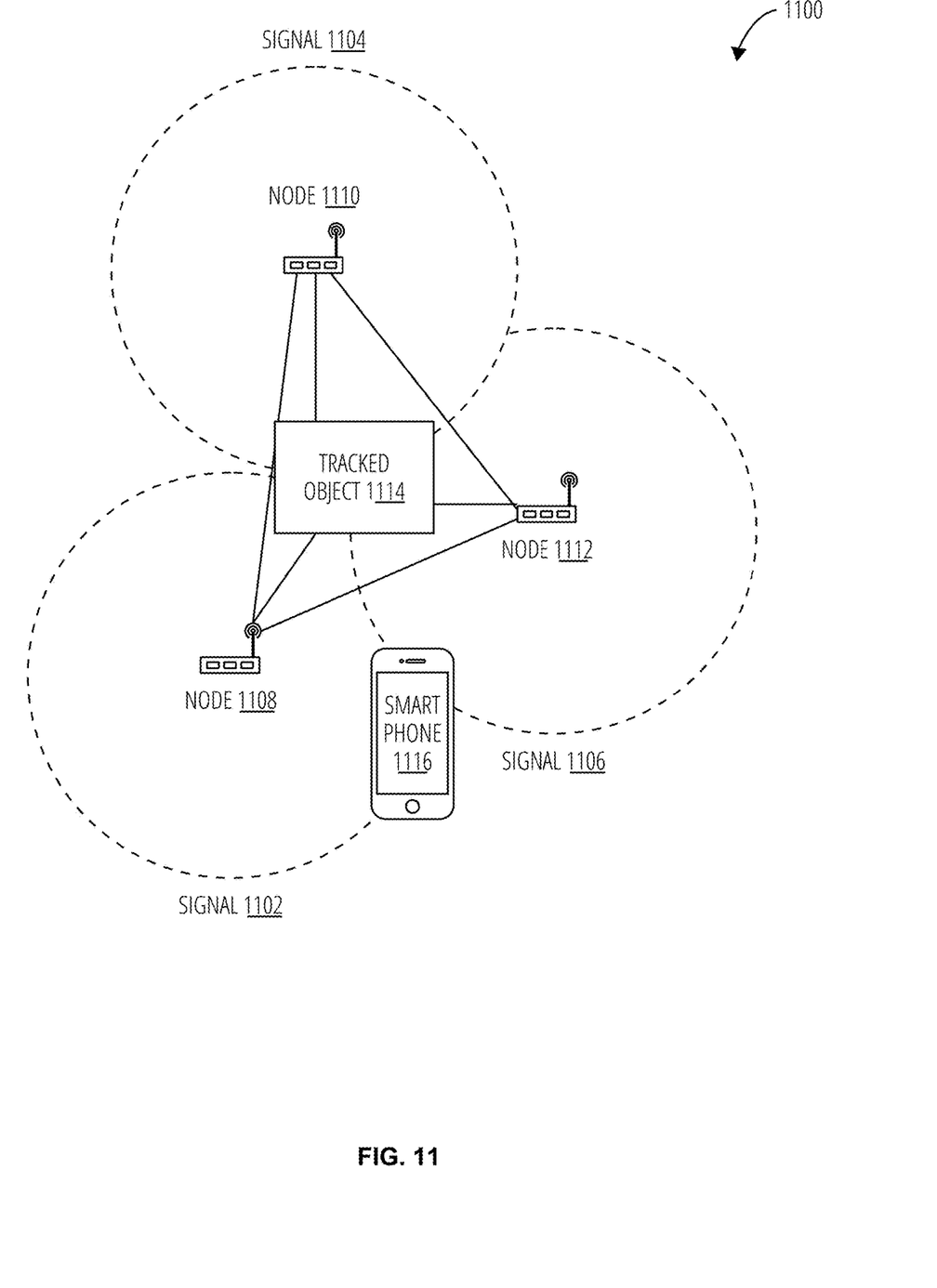
FIG. 11 illustrates an aspect of a system 1100 for integrating building automation with location awareness utilizing wireless mesh technology

Referring to FIG. 5, an embodiment of a sanitization verification process 500 begins by receiving a first location signal from a tag (block 502). A second location signal is then received from the tag (block 504). Whether a cleanliness threshold has been crossed by the tag is determined (decision block 506). This may be based on comparing the first location signal and the second location signal. If the cleanliness threshold was crossed, whether a proximity signal has been received from a sanitization device is determined (decision block 508). The system 1100 may be utilized to determine the first location signal, the second location signal, and whether a cleanliness threshold has been crossed.

Figure 6:
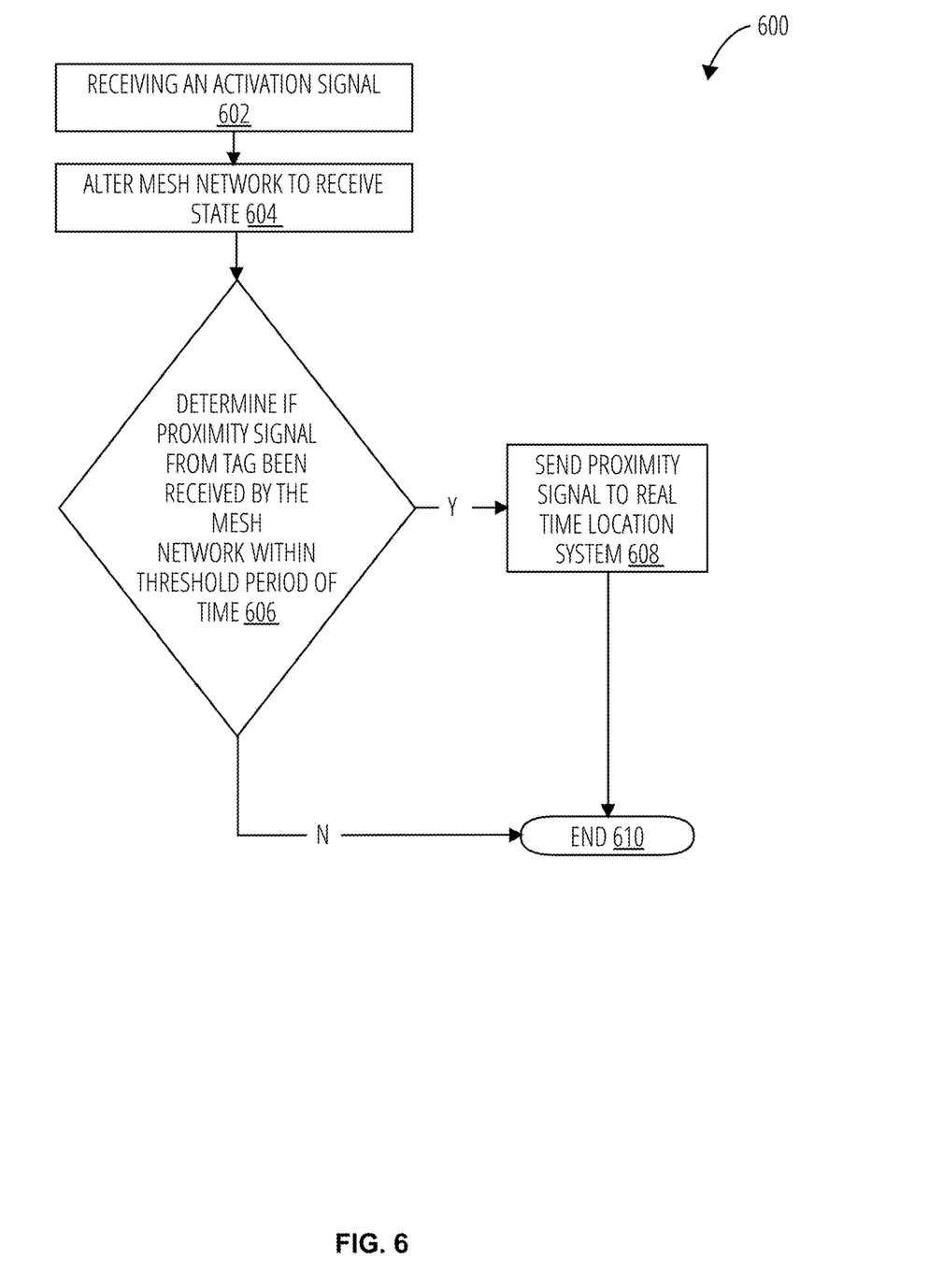
FIG. 6 illustrates an embodiment of a proximity signal detection process 600.

A proximity signal detection process 600 may be utilized to determine whether the proximity signal has been received, as depicted for example in FIG. 6. If the proximity signal has been received, compliance with sanitization is recorded (block 510). If the proximity signal was not received, non-compliance is recorded (block 512). After recording compliance or non-compliance, or if no cleanliness threshold was crossed, the sanitization verification process 500 ends (done block 514).

Referring to FIG. 6, an embodiment of a proximity signal detection process 600 begins by receiving an activation signal (block 602). A mesh network is then set to a receive state from a sleep state (block 604). Whether a proximity signal has been received from a tag during the period of time in which the mesh network is in the receive state is determined (decision block 606).

If so, the proximity signal is sent to a real time location system (block 608). After sending the proximity signal or determining that no proximity signal was received from a tag, the proximity signal detection process 600 ends (done block 610).

Figure 7:
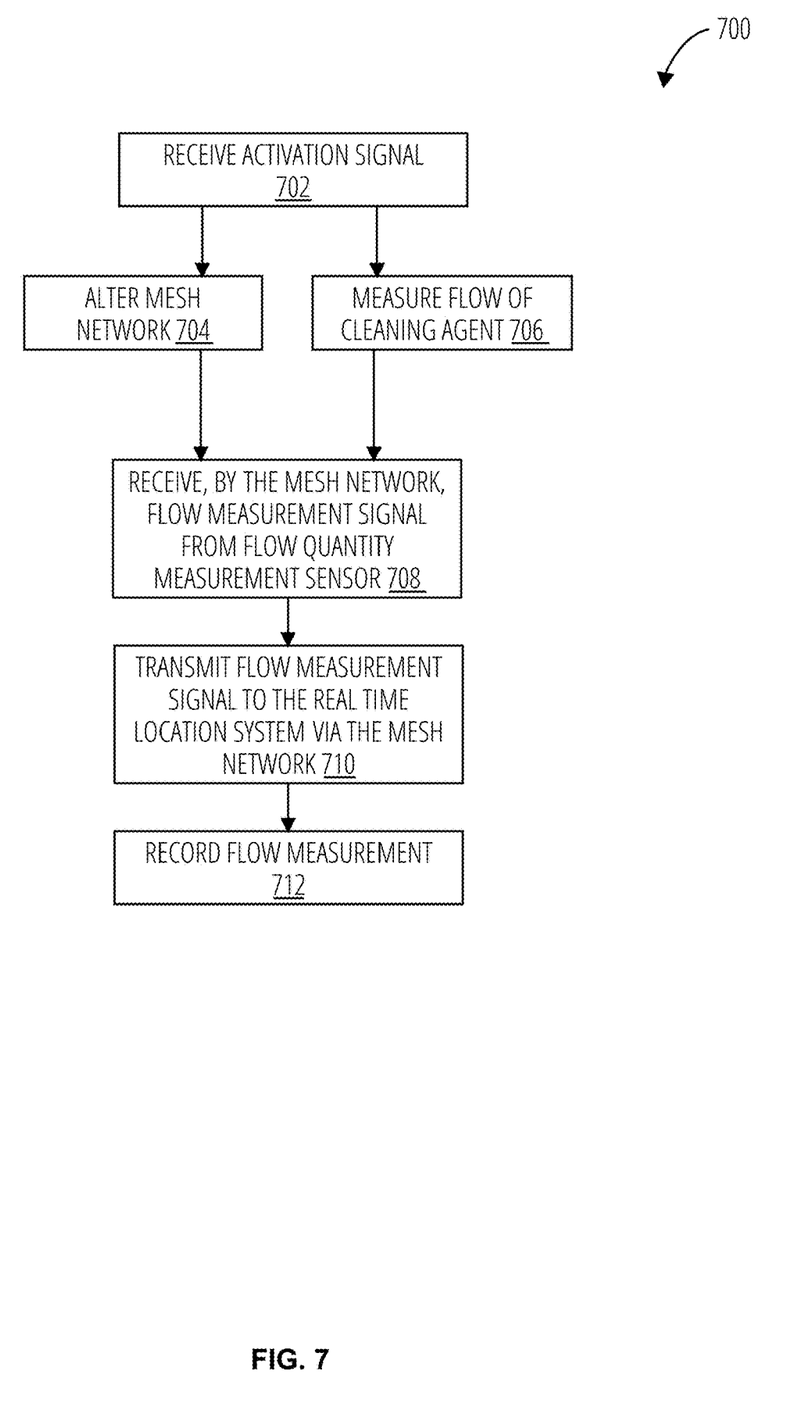
FIG. 7 illustrates an embodiment of a flow measurement process 700.

Referring to FIG. 7, the flow measurement process 700 receives an activation signal (block 702). The activation signal may be sent by a sanitization device and received by a mesh network. In response to receiving the activation signal, the mesh network is altered from a low-activity state to a high-activity receive state (block 704). The mesh network may remain in the high-activity receive state for a period of time. Additionally, a flow of cleaning agent is measured (block 706). The flow of the cleaning agent may be determined by a flow quantity measurement sensor. A flow measurement signal is then received by the mesh network from the flow quantity measurement sensor (block 708). The mesh network may be in the high-activity receive state when the flow measurement signal is received. The flow measurement signal is transmitted to a real time location system, which may be performed by the mesh network (block 710). The real time location system then records the flow measurement (block 712).

Figure 8:
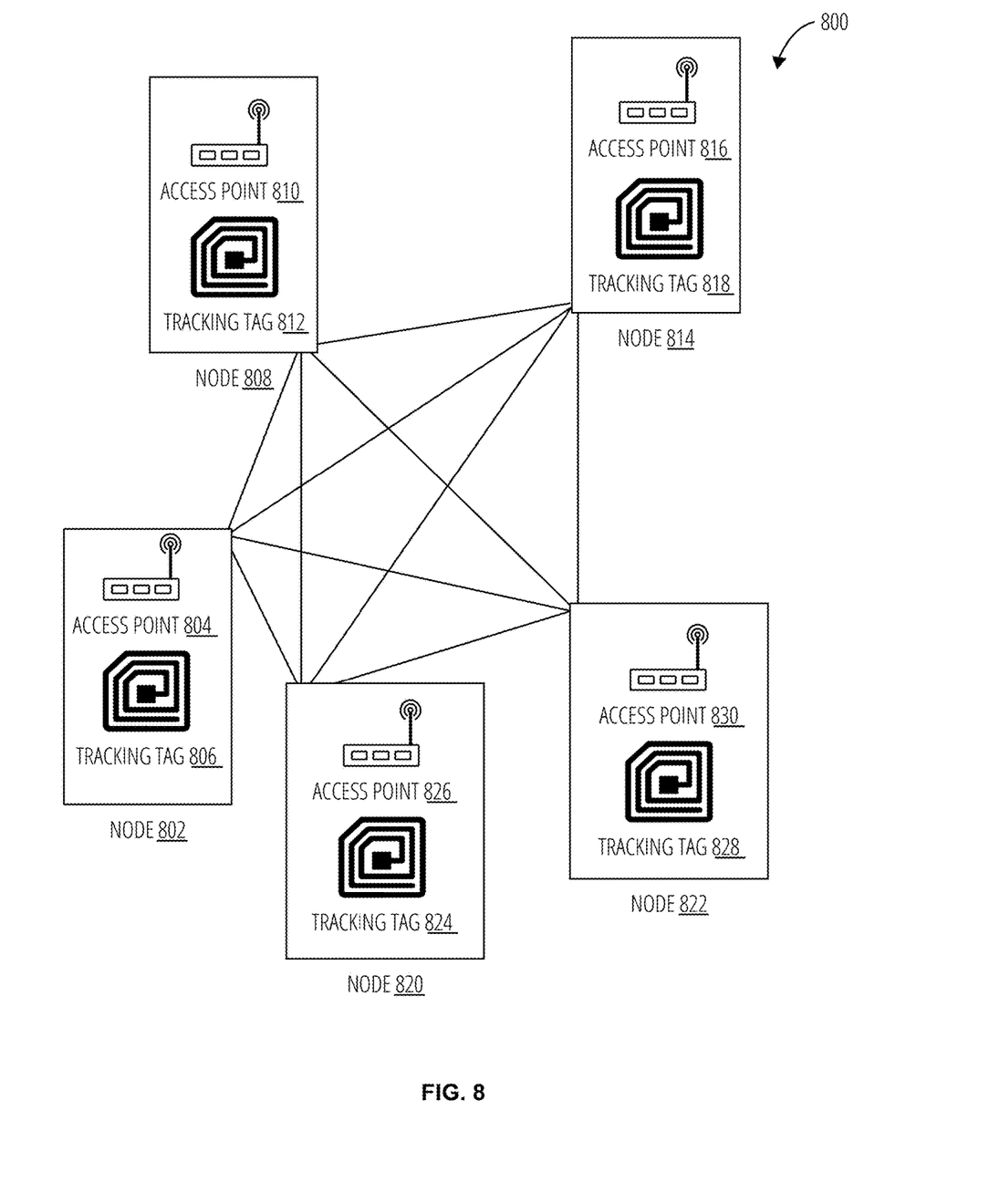
FIG. 8 illustrates an embodiment of a system 800 for integrating building automation with location awareness utilizing wireless mesh technology.

FIG. 8 illustrates an embodiment of a system 800 for integrating building automation with location awareness utilizing wireless mesh technology. The system 800 comprises the node 808, the node 814, the node 822, the node 802, and the node 820.

Each node includes a tracking tag and an access point to building automation systems. In this example, the node 808 comprises the tracking tag 812 and the access point 810, the node 814 comprises the tracking tag 818 and the access point 816, the node 822 comprises a tracking tag 828 and the access point 830, the node 820 comprises the tracking tag 824 and the access point 826, and the node 802 comprises the the tracking tag 806 and the access point 804.

The system 800 is merely one example of such a system and the number of nodes will vary according to implementation.

The system 800 may be utilized by the mesh network 208 to communicate data signals from the tag 206 and the sanitization device 300 to the real time location system 210.

Figure 9:
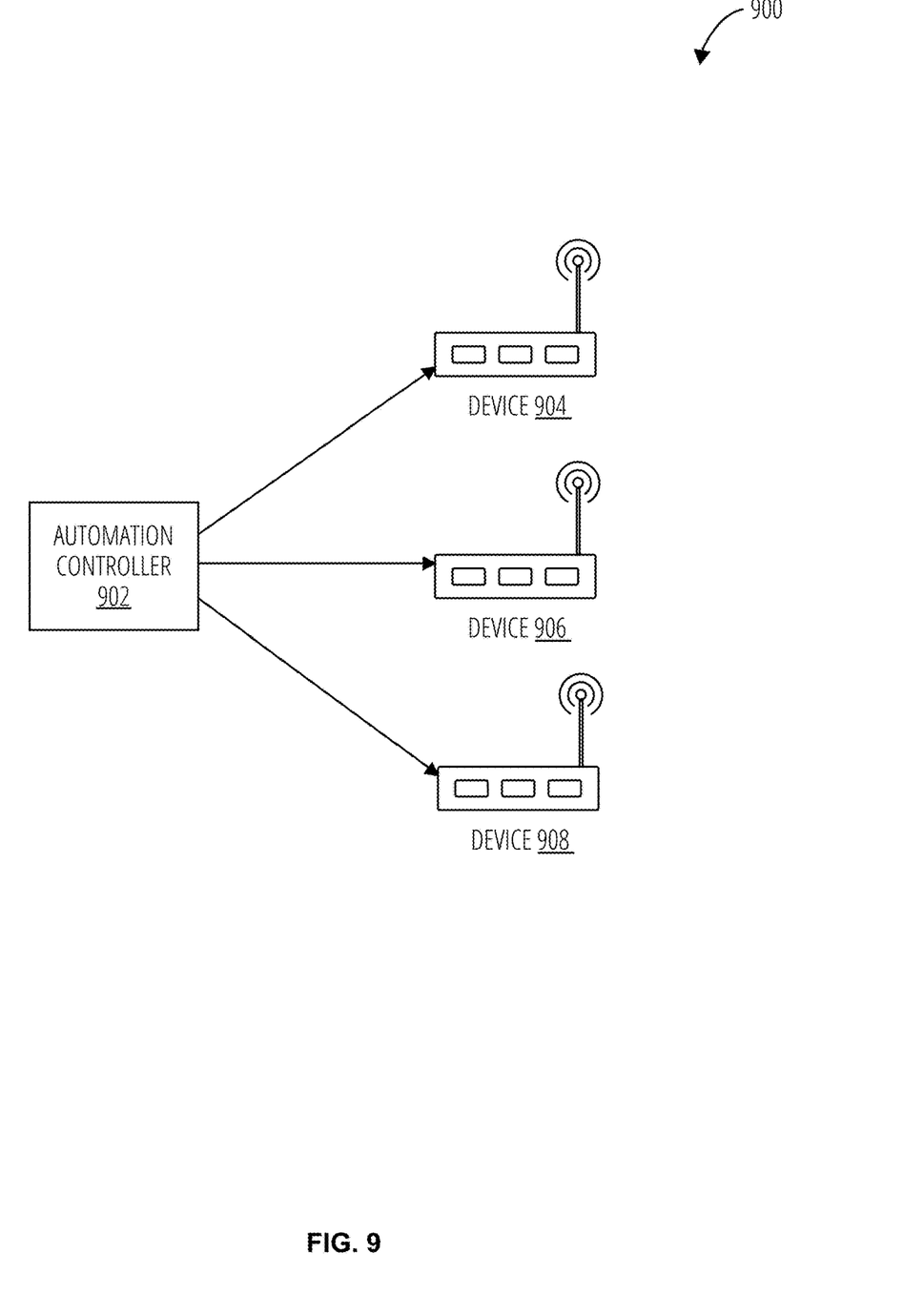
FIG. 9 illustrates an embodiment of a building automation and location awareness environment 900.

Referring now to FIG. 9, a building automation and location awareness environment 900 in one example includes a device 906, an automation controller 902, a device 904, and a device 908.

The building automation and location awareness environment 900 may be utilize to send control signals to devices such as the sanitization device 300. For example, the automation controller 902 may send a control signal to the sanitization device 300 to operate the notification device 306. In response to receiving the control signal, the notification device 306 may be activated.

Figure 10:
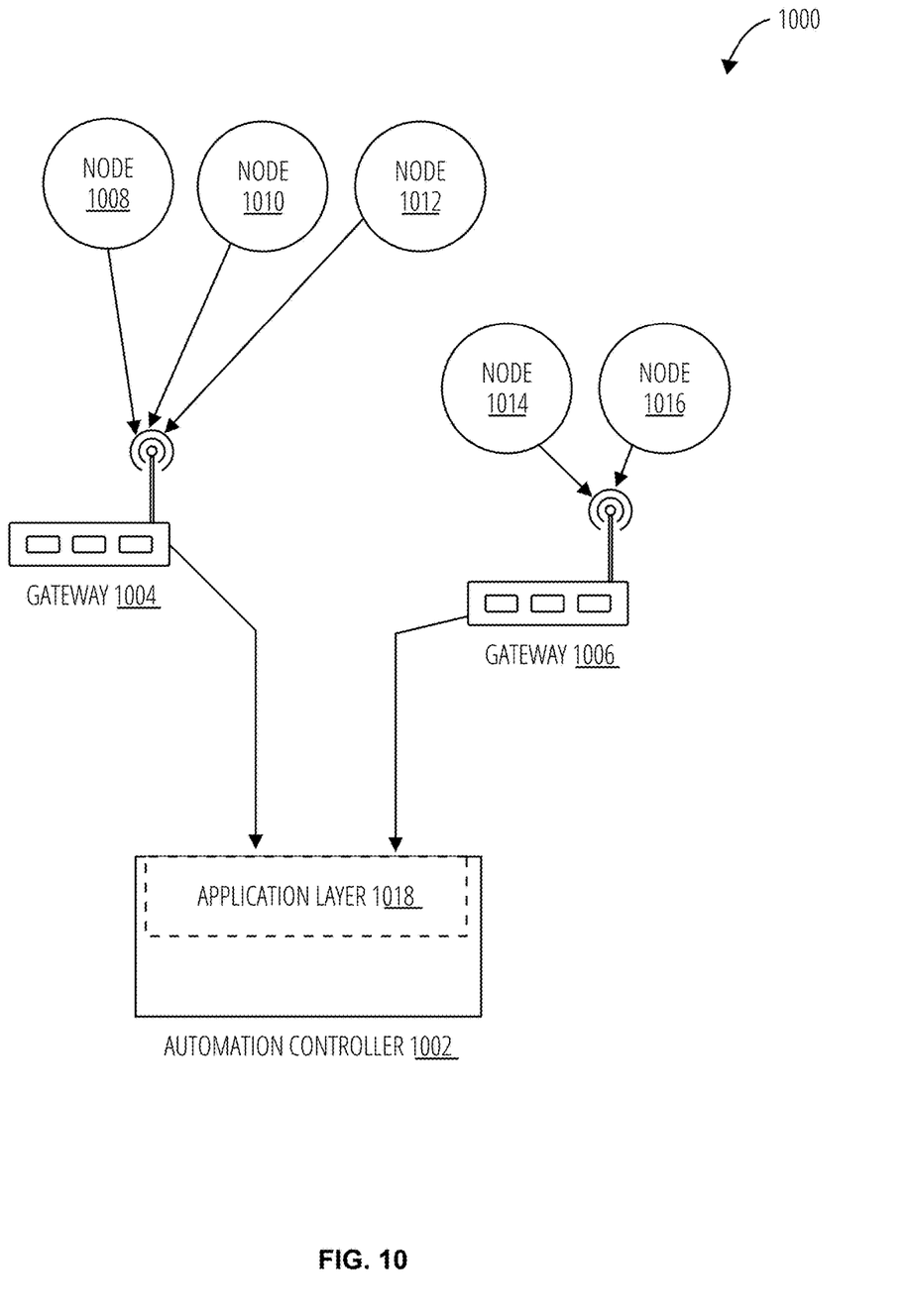
FIG. 10 illustrates an embodiment of a system 1000 for integrating building automation with location awareness utilizing wireless mesh technology.

FIG. 10 illustrates an embodiment of a system 1000 for integrating building automation with location awareness utilizing wireless mesh technology.

The system 1000 includes the node 1008, the node 1010, the node 1012, the node 1014, the node 1016, the gateway 1004, the gateway 1006, the application layer 1018 and the automation controller 1002.

The system 1000 may receive signals from the tag 206 and the sanitization device 300 at one or more of the node 1008, the node 1010, the node 1012, the node 1014, the node 1016. These signals are further transmitted to the gateway 1004 and/or the gateway 1006, as well as the automation controller 1002. Once received, the automation controller 1002 may perform operations in the application layer 1018. the operation may include determining the location of the tag 206, whether the tag 206 crossed a cleanliness threshold, and whether an activation signal was received from the sanitization device 300.

FIG. 11 illustrates an embodiment of a system 1100 for integrating building automation with location awareness utilizing wireless mesh technology.

The system 1100 includes a tracked object 1114, a node 1108, a node 1110, a node 1112, a signal 1102, a signal 1104, a signal 1106, and a smart phone 1116.

The tracked object 1114 may be a tag 206. Nodes, such as the node 1108, the node 1110, and the node 1112, may be located in the first zone 202 and the second zone 204. These nodes communicate to the automation controller 1002 location data for the application layer 1018 to determine the location of the tracked object 1114 (e.g., the tag 206). The smart phone 1116 may be utilized as the automation controller 1002 in some embodiments.

Figure 12:
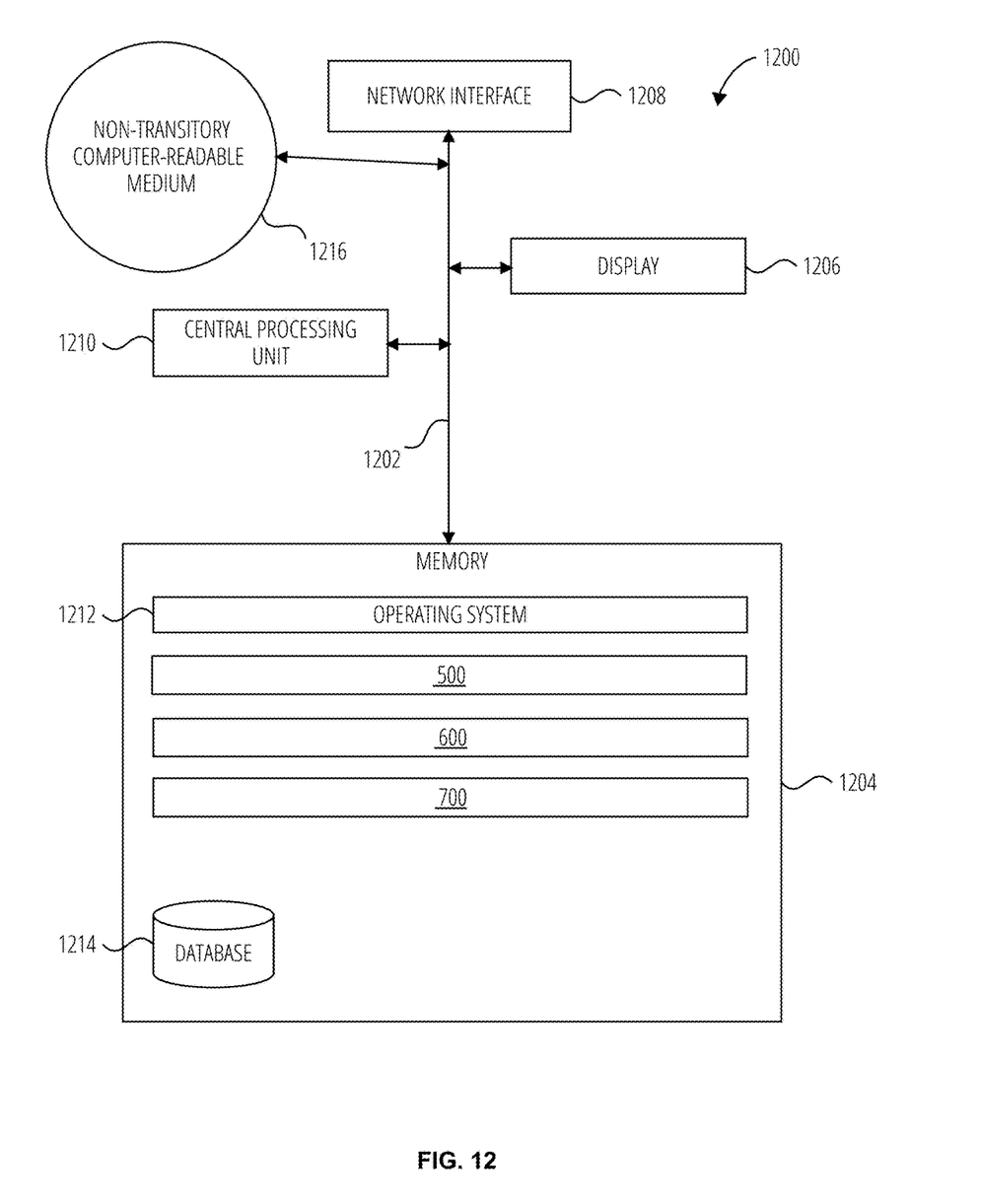
FIG. 12 illustrates a system 1200 in accordance with one embodiment.

FIG. 12 illustrates several components of an exemplary system 1200 in accordance with one embodiment. In various embodiments, system 1200 may include a computing device that is capable of performing operations such as those described herein (e.g., a dispenser). In some embodiments, system 1200 may include many more components than those shown in FIG. 12. However, it is not necessary that all of these generally conventional components be shown in order to disclose an illustrative embodiment. Collectively, the various tangible components or a subset of the tangible components may be referred to herein as "logic" configured or adapted in a particular way, for example as logic configured or adapted with particular software or firmware.

In various embodiments, system 1200 may comprise one or more physical and/or logical devices that collectively provide the functionalities described herein. In some embodiments, system 1200 may comprise one or more replicated and/or distributed physical or logical devices.

In some embodiments, system 1200 may comprise one or more computing resources provisioned from a "cloud computing" provider, for example, Amazon Elastic Compute Cloud ("Amazon EC2"), provided by Amazon.com, Inc. of Seattle, Wash.; Sun Cloud Compute Utility, provided by Sun Microsystems, Inc. of Santa Clara, Calif.; Windows Azure, provided by Microsoft Corporation of Redmond, Wash., and the like.

System 1200 includes a bus 1202 interconnecting several components including a network interface 1208, a display 1206, a central processing unit 1210, and a memory 1204.

Memory 1204 generally comprises a random access memory ("RAM") and permanent non-transitory mass storage device, such as a hard disk drive or solid-state drive. Memory 1204 stores an operating system 1212.

These and other software components may be loaded into memory 1204 of system 1200 using a drive mechanism (not shown) associated with a non-transitory computer-readable medium 1216, such as a floppy disc, tape, DVD/CD-ROM drive, memory card, or the like.

Memory 1204 also includes database 1214. In some embodiments, system 1200 may communicate with database 1214 via network interface 1208, a storage area network ("SAN"), a high-speed serial bus, and/or via the other suitable communication technology.

In some embodiments, database 1214 may comprise one or more storage resources provisioned from a "cloud storage" provider, for example, Amazon Simple Storage Service ("Amazon S3"), provided by Amazon.com, Inc. of Seattle, Wash., Google Cloud Storage, provided by Google, Inc. of Mountain View, Calif., and the like.

Those having skill in the art will appreciate that there are various logic implementations by which processes and/or systems described herein can be effected (e.g., hardware, software, or firmware), and that the preferred vehicle will vary with the context in which the processes are deployed. If an implementer determines that speed and accuracy are paramount, the implementer may opt for a hardware or firmware implementation; alternatively, if flexibility is paramount, the implementer may opt for a solely software implementation; or, yet again alternatively, the implementer may opt for some combination of hardware, software, or firmware. Hence, there are numerous possible implementations by which the processes described herein may be effected, none of which is inherently superior to the other in that any vehicle to be utilized is a choice dependent upon the context in which the implementation will be deployed and the specific concerns (e.g., speed, flexibility, or predictability) of the implementer, any of which may vary. Those skilled in the art will recognize that optical aspects of implementations may involve optically-oriented hardware, software, and or firmware.

Those skilled in the art will appreciate that logic may be distributed throughout one or more devices, and/or may be comprised of combinations memory, media, processing circuits and controllers, other circuits, and so on. Therefore, in the interest of clarity and correctness logic may not always be distinctly illustrated in drawings of devices and systems, although it is inherently present therein. The techniques and procedures described herein may be implemented via logic distributed in one or more computing devices. The particular distribution and choice of logic will vary according to implementation.

The foregoing detailed description has set forth various embodiments of the devices or processes via the use of block diagrams, flowcharts, or examples. Insofar as such block diagrams, flowcharts, or examples contain one or more functions or operations, it will be understood as notorious by those within the art that each function or operation within such block diagrams, flowcharts, or examples can be implemented, individually or collectively, by a wide range of hardware, software, firmware, or virtually any combination thereof. Portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more processing devices (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

In a general sense, those skilled in the art will recognize that the various aspects described herein which can be implemented, individually or collectively, by a wide range of hardware, software, firmware, or any combination thereof can be viewed as being composed of various types of circuitry.

Those skilled in the art will recognize that it is common within the art to describe devices or processes in the fashion set forth herein, and thereafter use standard engineering practices to integrate such described devices or processes into larger systems. At least a portion of the devices or processes described herein can be integrated into a network processing system via a reasonable amount of experimentation. Various embodiments are described herein and presented by way of example and not limitation.

What is claimed:

1. A sanitation compliance system comprising:
a mesh network including client nodes that are configured to send data, receive data, and relay data for the mesh network;
a sanitation device, wherein the sanitation device is a client node in the mesh network, the sanitation device comprising:
a proximity sensor;
an activation sensor responsive to the proximity sensor to generate an activation signal;
a transmitter responsive to the activation sensor to communicate to the mesh network an event signal comprising the activation signal and a dispensing indication of a cleaning agent; and
a real-time location system to determine a change in location of a mobile tag from a first zone to a second zone where entry to the second zone is associated with use of the sanitation device; and
verification logic to process the event signal from the transmitter and to determine an association of the event signal with the change in location of the mobile tag.

2. The sanitation compliance system of claim 1, the sanitation device further comprising a flow measurement sensor to measure an amount of the cleaning agent dispensed.

3. The sanitation compliance system of claim 2, the event signal further comprising an amount of the cleaning agent dispensed from the sanitation device as detected by the flow measurement sensor.

4. The sanitation compliance system of claim 1, the verification logic to further to apply the event signal to determine a compliance by a user of the mobile tag with the amount of cleaning agent dispensed associated with the second zone.

5. The sanitation compliance system of claim 1, wherein the proximity sensor is an infrared sensor.

6. A sanitation compliance system comprising:
a mesh network;
a sanitation device comprising:
an activation sensor, wherein the activation sensor generates an activation signal upon operation of the sanitation device;
a transmitter responsive to the activation sensor to communicate to the mesh network an event signal comprising the activation signal and a dispensing indication of a cleaning agent;
a flow measurement sensor to measure an amount of the cleaning agent dispensed; and
a real-time location system to determine a change in location of a mobile tag from a first zone to a second zone where entry to the second zone is associated with use of the sanitation device; and
verification logic to process the event signal from the transmitter and to determine an association of the event signal with the change in location of the mobile tag.

7. The sanitation compliance system of claim 6, wherein the activation sensor utilizes at least one or more of an infrared sensor, mechanical action, or haptic input.

* * * * *